United States Patent [19]

Doi

[11] Patent Number: 5,223,438
[45] Date of Patent: Jun. 29, 1993

[54] AGENT COMPOSITION FOR DETECTING REDOX REACTION

[75] Inventor: Kenichi Doi, Kurita, Japan

[73] Assignee: Kyoto Daiichi Kagaku Co., Ltd., Kyoto, Japan

[21] Appl. No.: 770,926

[22] Filed: Oct. 4, 1991

[30] Foreign Application Priority Data

Oct. 8, 1990 [JP] Japan .................. 2-270952

[51] Int. Cl.$^5$ .................. G01N 1/00; C12Q 1/00
[52] U.S. Cl. .................. 436/175; 435/4; 435/14; 435/28; 436/73; 436/135; 436/164; 436/904
[58] Field of Search .............. 436/164, 825, 175, 904, 436/177, 135, 73, 80, 66; 423/112, 111; 435/4, 14, 28

[56] References Cited

U.S. PATENT DOCUMENTS

| | | | |
|---|---|---|---|
| 3,411,887 | 11/1968 | Ku et al. | 422/57 |
| 4,288,541 | 9/1981 | Magers et al. | 436/175 |
| 4,295,853 | 10/1981 | Kasahara | 436/71 |
| 4,438,080 | 3/1984 | McEuen et al. | 423/112 |
| 4,587,220 | 5/1986 | Mayambala-Mwanika et al. | 436/66 |
| 4,743,559 | 5/1988 | Koever et al. | 436/175 |
| 4,957,872 | 9/1990 | Koever et al. | 436/175 |
| 5,079,140 | 1/1992 | Albarella et al. | 435/4 |

FOREIGN PATENT DOCUMENTS 0141244  5/1985  European Pat. Off. .
56-109595  8/1981  Japan .

OTHER PUBLICATIONS

Steven S. Zumdahl, Chemistry, 1986, p. 774.

*Primary Examiner*—James C. Housel
*Assistant Examiner*—Long V. Le
*Attorney, Agent, or Firm*—Birch, Stewart, Kolasch & Birch

[57] ABSTRACT

An agent composition for detecting a redox reaction comprising a redox reagent system, iodic acid or an iodate, and a monovalent thallium compound, which suppresses adverse influence of liberated iodine and provides accurate diagnosis results.

14 Claims, 10 Drawing Sheets

TMBZ pH5 Glu=0--1g/dl

With Tl

AGENT COMPOSITION FOR DETECTING REDOX REACTION

BACKGROUND OF THE INVENTION

1. Field of the Invention

The present invention relates to an agent composition for detecting a redox reaction. More particularly, the present invention relates to an agent composition that can suppress or remove the adverse influence of iodine which is liberated when such an agent for detecting a redox reaction contains iodic acid or an iodate for removing a reducing substance.

2. Description of the Related Art

Various diagnostic agents are known for detecting various substances in a body based on redox reactions.

Since a reducing substance present in a reaction system, such as ascorbic acid, interferes with the redox reaction, many measures for preventing or avoiding such interference have been proposed. Japanese Patent Publication No. 15280/1989 (corresponding to Japanese Patent Kokai Publication No. 109595/1981) discloses pretreatment of a sample to be analyzed with iodic acid or an iodate at pH of 3 to 5. Japanese Patent Publication No. 4861/1990 (corresponding to U.S. Pat. Nos. 4,743,559 and 4,957872 and EP-A-037 056) discloses a diagnostic agent for detecting a redox reaction which can avoid the influence of ascorbic acid by the presence of iodic acid or an iodate.

However, the pretreatment of the former method makes the analysis (diagnostic procedures) complicated and is less preferred.

When the latter diagnostic agent, which removes the reducing substance with iodic acid or the iodate, an accurate diagnosis cannot be performed by using a conventional Trinder's reagent. This is because the iodine which is liberated through a reaction of the iodate with ascorbic acid serves to oxidize the Trinder's reagent and thus colors the background to give a false positive result.

At pH of less than 5, it is possible to remove not only ascorbic acid but also other reducing substances such as bilirubin, cysteine or aminopyrin with an iodate. However, at pH of less than 5, an influence of the liberated iodine increases so that, with any color reagent, it is impossible to avoid this influence. When pH is further decreased, the iodine is liberated in the absence of ascorbic acid and oxidizes the color reagent to color the background of a test piece.

As explained above, a cause of the adverse influence on the diagnostic agent is an oxidizing property of the liberated iodine.

If there were a method for quickly capturing the liberated iodine before it influences the color reagent, the adverse influence of the liberated iodine could be excluded.

SUMMARY OF THE INVENTION

An object of the present invention is to provide a novel agent composition for detecting a redox reaction, which contains iodic acid or an iodate for removing a reducing substance and which can avoid the adverse influence of liberated iodine.

According to the present invention, there is provided an agent composition for detecting a redox reaction, which comprises a redox reagent system, iodic acid or an iodate, and a monovalent thallium compound.

DETAILED DESCRIPTION OF THE INVENTION

Figure 1A:
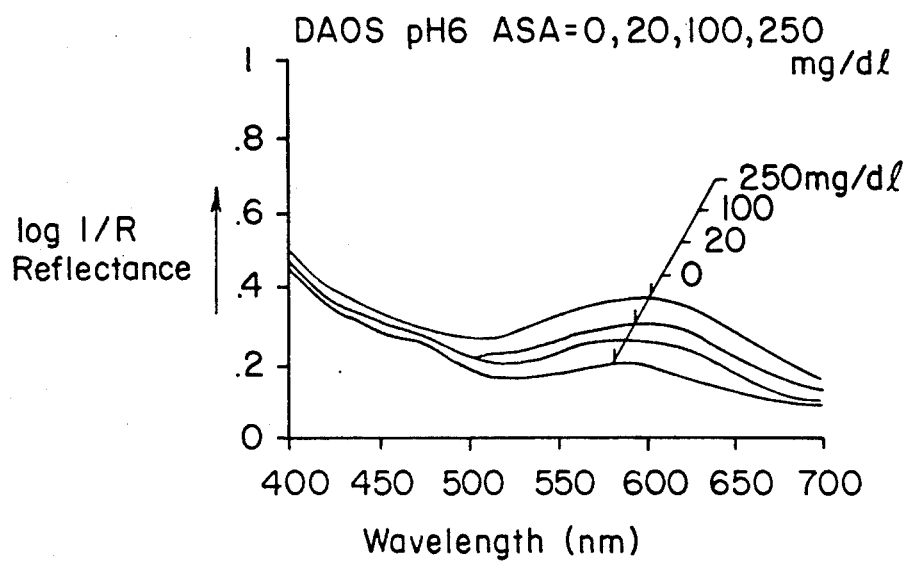
FIGS. 1A to 1H are graphs showing the change of the background by ascorbic acid in Example 1.
Figure 1B:
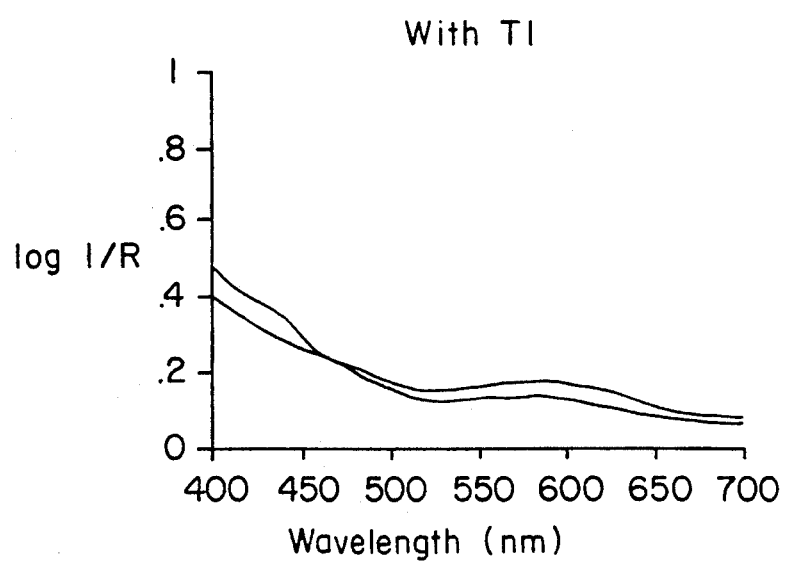
Figure 1C:
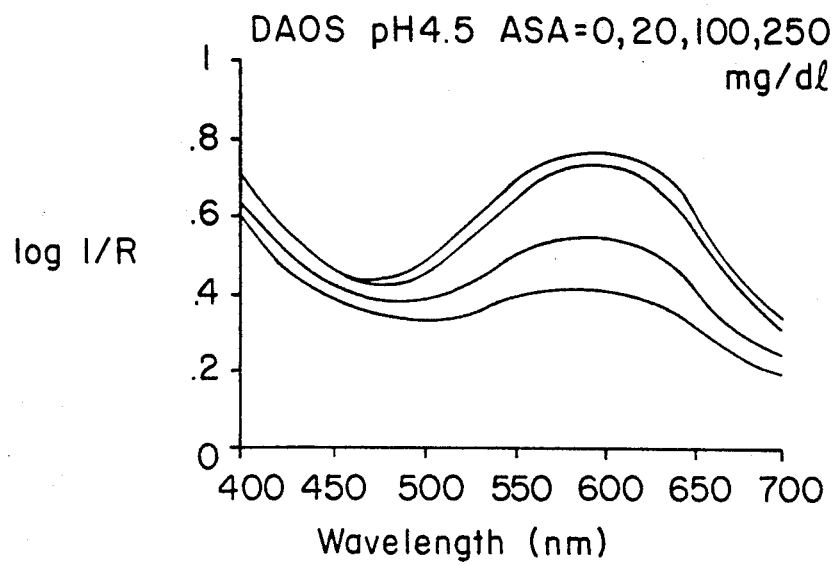
Figure 1D:
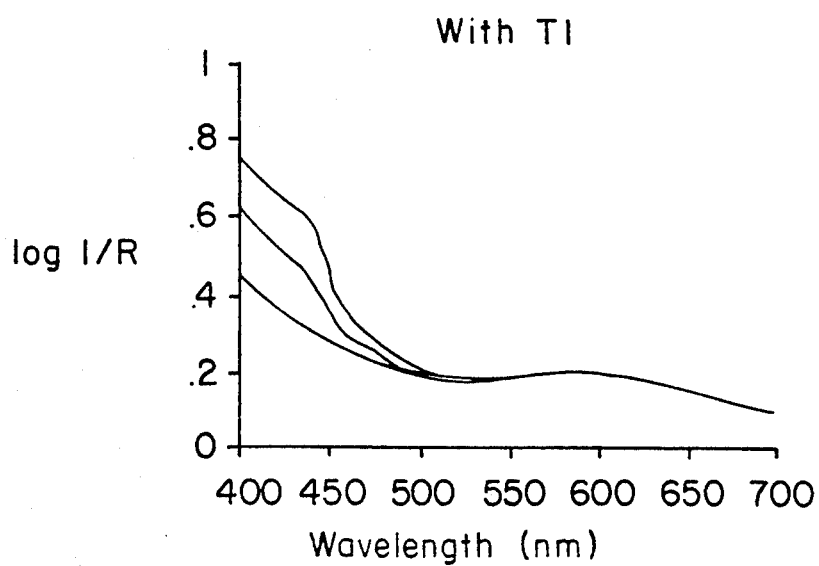
Figure 1E:
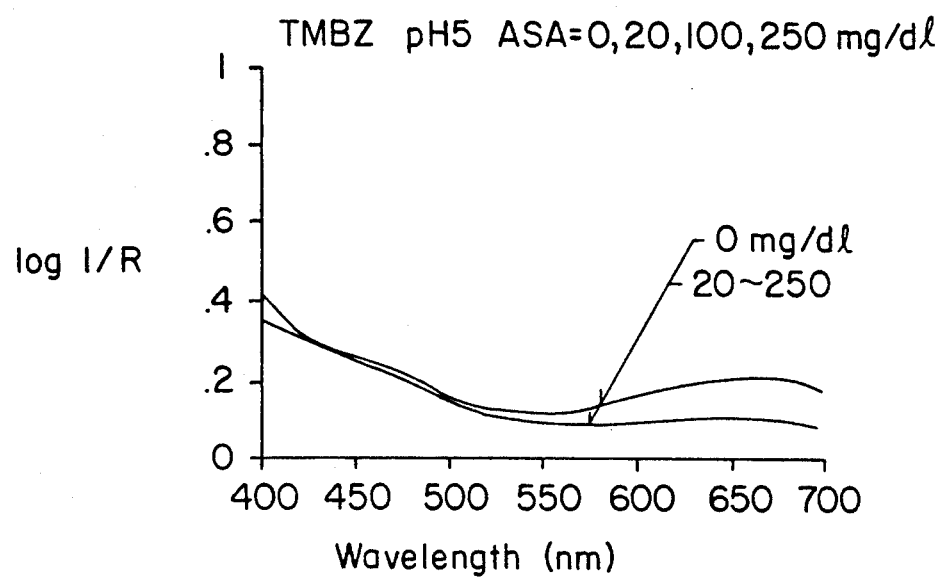
Figure 1F:
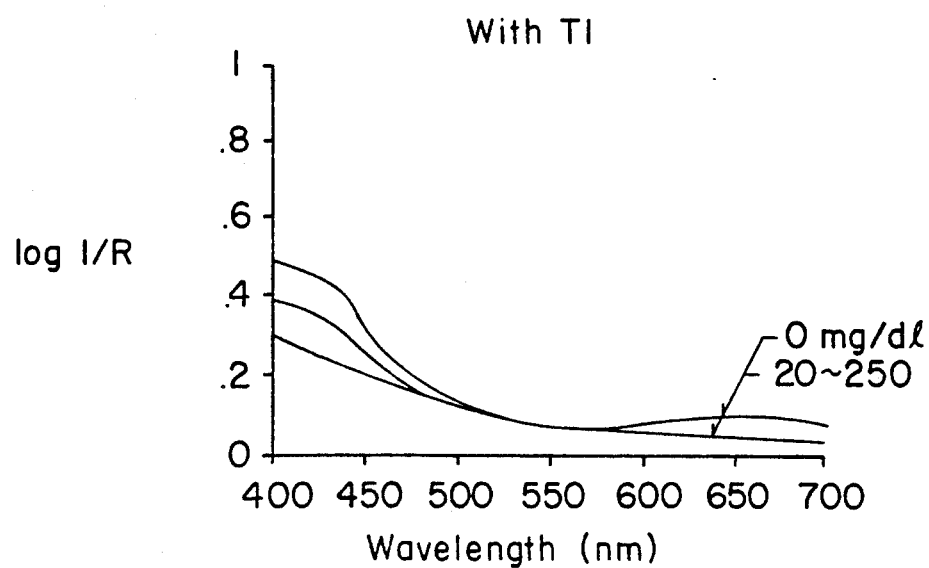
Figure 1G:
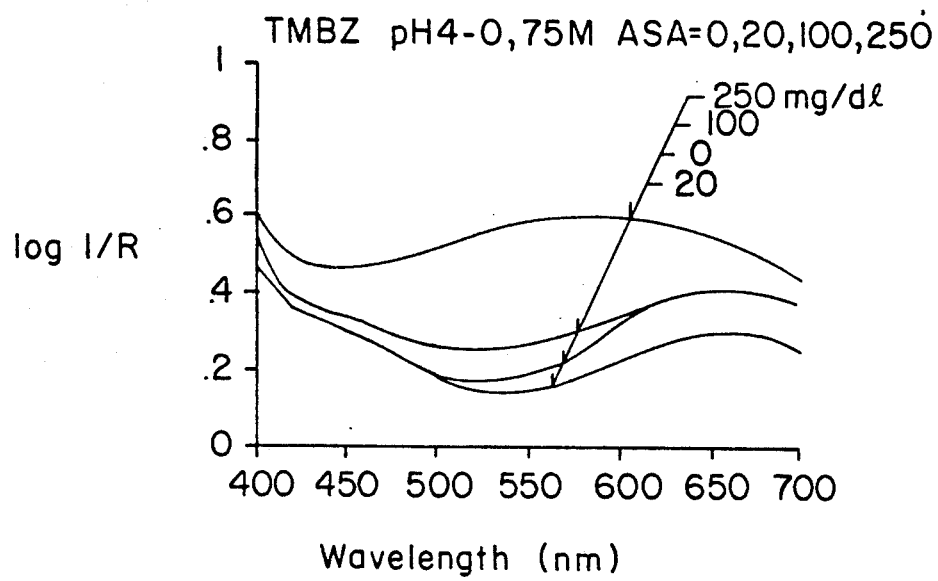
Figure 1H:
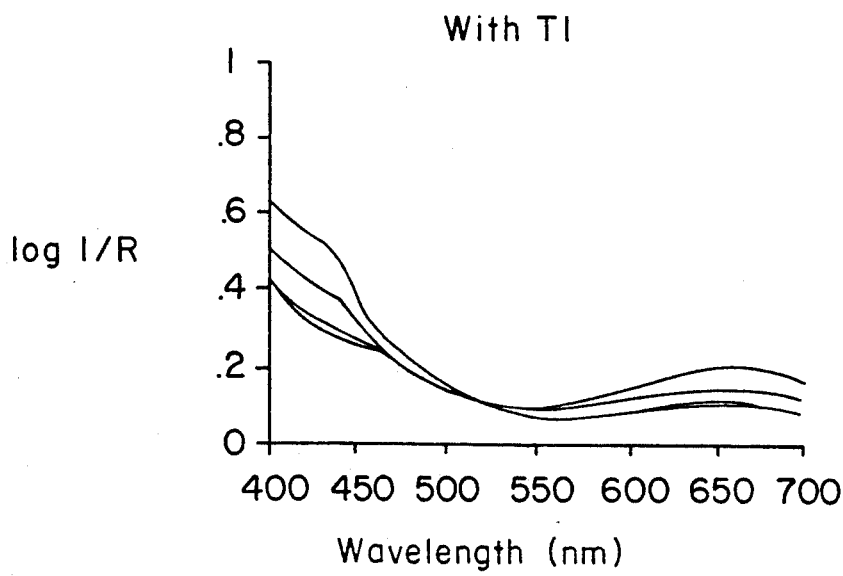
Figure 2A:
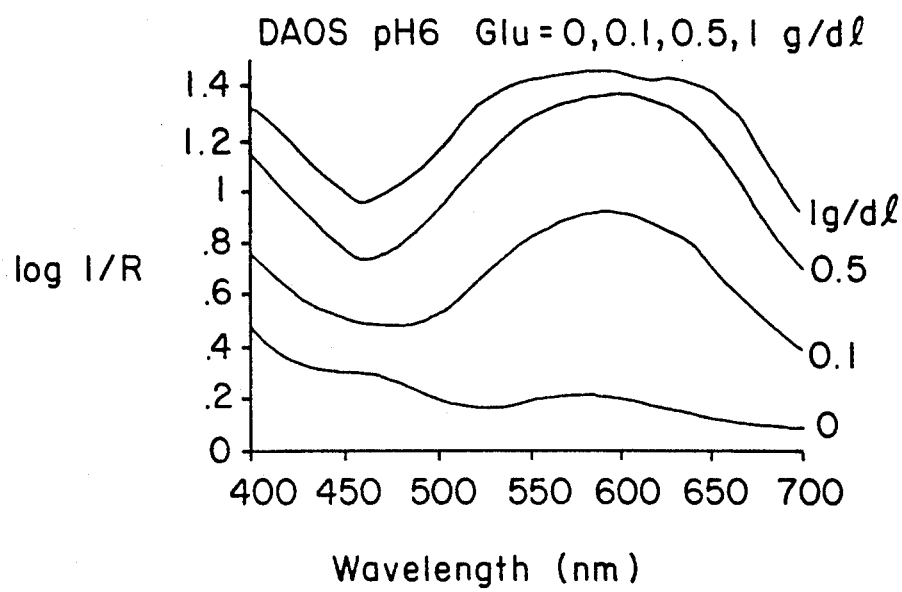
FIGS. 2A to 2H are graphs showing sensitivities in Example 1.
Figure 2B:
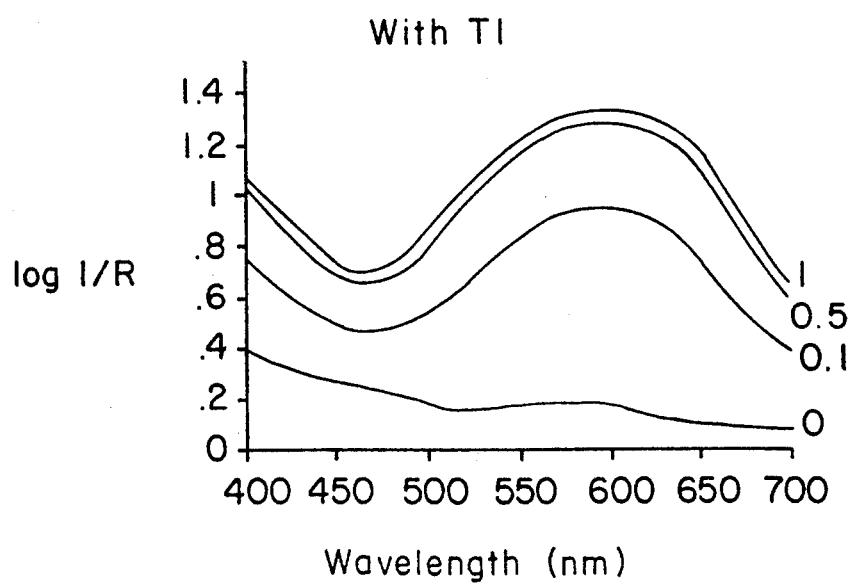
Figure 2C:
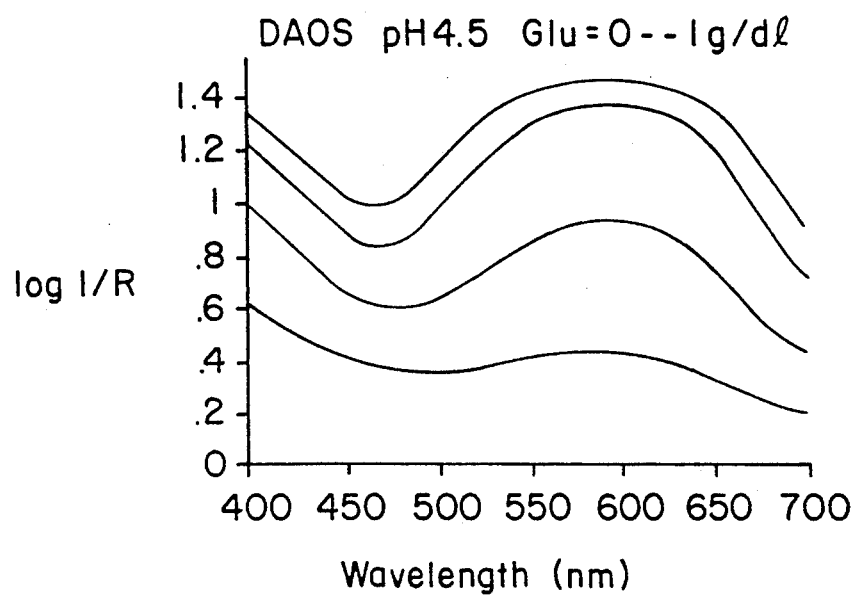
Figure 2D:
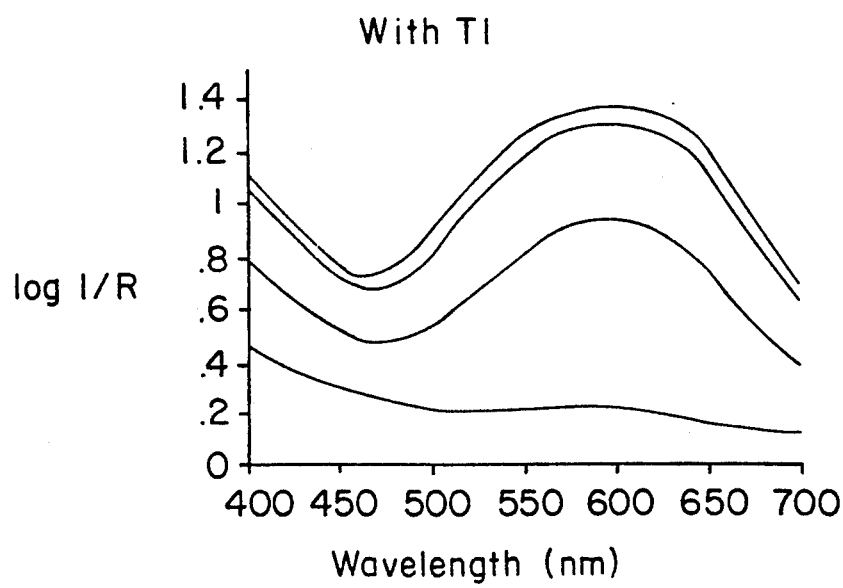
Figure 2E:
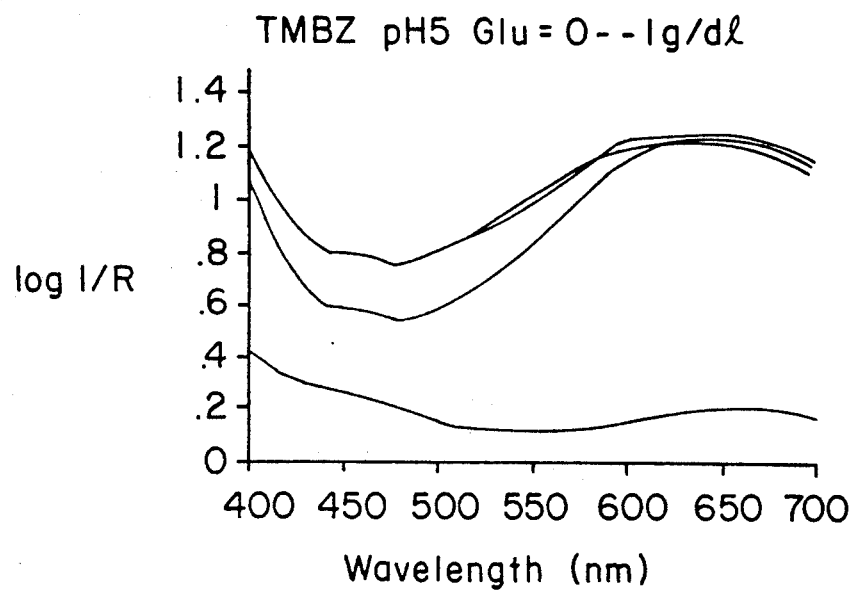
Figure 2F:
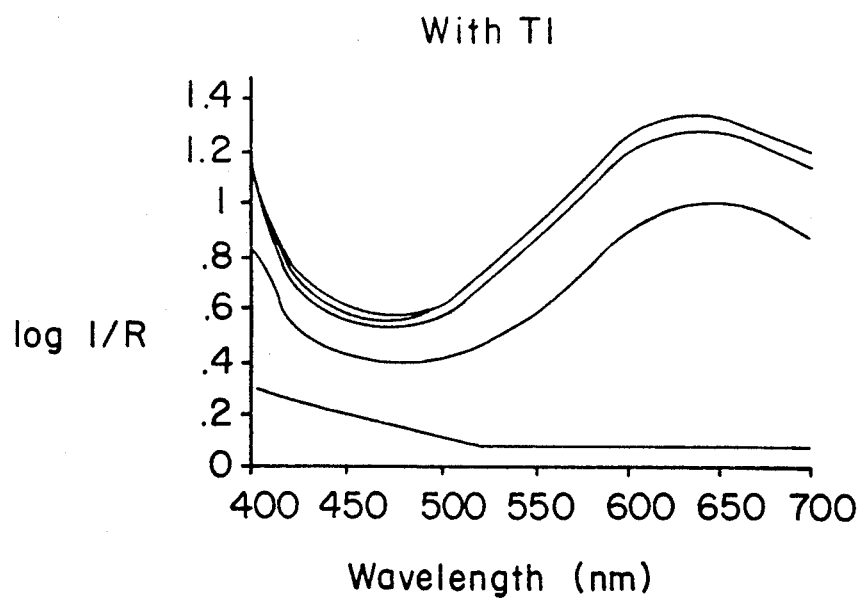
Figures 2G, 2H:
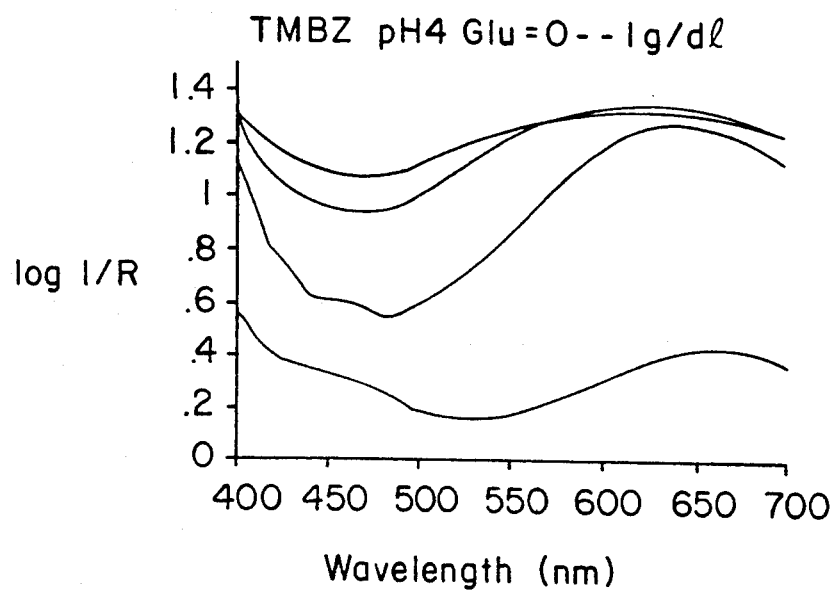

In general, a reducing property of iodide is deteriorated by the addition of sodium thiosulfate and the like. However, since a thiosulfate itself has a strong reducing property, it also decomposes iodic acid or the iodate.

When the monovalent thallium compound is added in a system for removing the reducing substances with iodic acid or the iodate, the liberated iodine is effectively trapped and the diagnostic agent has improved utility.

A reaction mechanism with which the monovalent thallium compound traps the iodine is not the oxidationreduction reaction but an ionic reaction. In addition, since thallium iodide formed by the ionic reaction is a hardly soluble yellow compound, reliberation of iodide ions can be prevented. Since the formed compound is yellow, it has no material influence on optical detection in an instrumental analysis. When a test paper is colored with a yellow dye, the color change through the redox reaction can be detected visually.

As described above, the use of the monovalent thallium compound has various advantages in the diagnostic agent composition. But, since the monovalent thallium compound is a strong oxidizing agent, it is assumed that such strong oxidizing property may have some adverse influence on the reaction system. Unexpectedly, the oxidizing property of the monovalent thallium compound never adversely affects the analysis in a reaction time for analysis. Further, the monovalent thallium compound does not decompose ascorbic acid. In this connection, a trivalent thallium compound has some adverse influences on the reaction system due to its oxidizing property and cannot be used.

In the present invention, any of the monovalent thallium compounds may be used. Among the compounds, salts with inorganic or organic acids are preferred. Specific examples of the monovalent thallium compound are thallium (I) chloride, thallium (I) sulfate and thallium (I) acetate.

An amount of the monovalent thallium compound is from 0.1 to 20 g, preferably from 1 to 10 g per 100 g of the reagent composition.

The redox reagent system to be used in the present invention may be any of conventionally used ones. Examples are disclosed in above described Japanese Patent Publication No. 4861/1990 and its corresponding US Patent and EP Patent Publication.

Examples of the iodate are potassium iodate, sodium iodate, magnesium iodate, ammonium iodate, etc. and a mixture thereof.

The redox reagent system and iodic acid or the iodate may be used in the same manner and the same amounts as in the conventional composition.

When the agent composition of the present invention is used, pH of the reaction system is not critical, and even pH of 5 or less may be used, though higher pH can be used.

When a benzidine derivative is used as a color reagent, pH is preferably in a range between 3 and 8. When the Trinder's reagent is used as a color reagent, pH is preferably in a range between 4 and 8.

The effects achieved by the present invention are as follows:

Since the monovalent thallium compound is used, it is possible to use the generally used Trinder's reagent in the reagent composition (diagnostic agent) in which the reducing substances are removed by iodic acid or the iodate.

The pH range in the case where the Trinder's reagent is used is from 4 to 8. Then, it is possible to remove the reducing substances such as bilirubin, cysteine and aminopyrin. When the benzidine derivative color reagent is used, pH can be reduced down to 3 so that the reducing substances such as bilirubin, cysteine and aminopyrin can be removed.

The addition of the monovalent thallium compound can suppress the coloring of the background of the test paper (an amount of ascorbic acid being zero (0)).

PREFERRED EMBODIMENTS OF THE INVENTION

The present invention will be illustrated by the following Examples.

EXAMPLE 1

A test paper having a formulation of Table 1 was prepared, and change of the background of the test paper was examined under the following conditions:
  Sizes of the test paper: 5 mm × 5 mm square
  Measuring procedures: Dipping and reading
  Measuring time: After one minutes
  Apparatus: A photoelectric colorimeter (SZ-Σ80 manufactured by Nippon Denshoku Kabushikikaisha)
  Sample: An aqueous solution of ascorbic acid (concentration: 0, 20, 100 and 250 mg/dl)

The results are shown in FIGS. 1A to 1H, in which the vertical axes are in terms of LogI/R.

Then, the sensitivity was examined by the same procedures as above except that, as a sample, a glucose solution (concentration: 0, 0.1, 0.5 and 1 g/dl) was used. The results are shown in FIGS. 2A to 2H.

Figure 3:
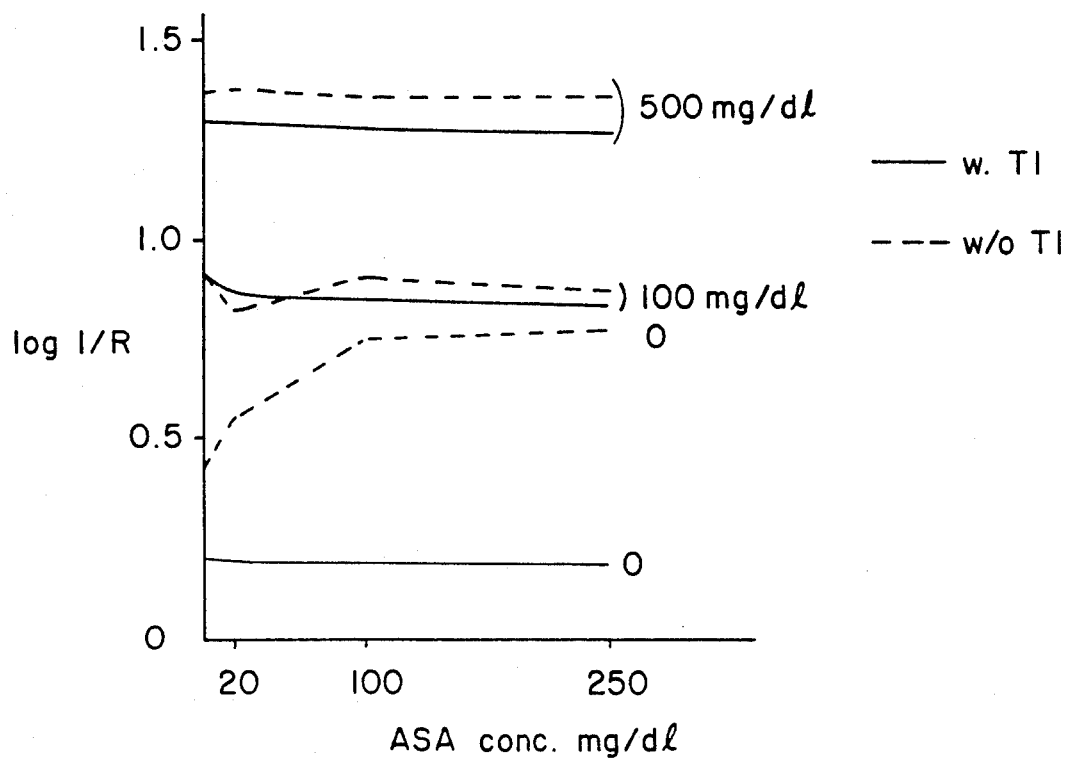
FIG. 3 is a graph showing the change of reflectance by ascorbic acid in Example 1.

To examine whether or not a coloring degree by the liberated iodine in the reaction of ascorbic acid and the iodate was suppressed by the thallium compound, the following experiment was carried out. That is, the suppression of coloring was determined by the same procedures as above but using the test paper of the formulation No. 3 or 4 in Table 1 and a solution of glucose having a concentration of 0, 100 or 500 mg/dl to which ascorbic acid was added at a concentration of 0, 20, 100 or 250 mg/dl. The results are shown in FIG. 3.

TABLE 1

| Formulation of Test Papers | | | | | | | | |
|---|---|---|---|---|---|---|---|---|
| | Formulation No. | | | | | | | |
| | 1 | 2 | 3 | 4 | 5 | 6 | 7 | 8 |
| (First layer) | | | | | | | | |
| Glucose oxidase (kU) | 16 | ← | ← | ← | ← | ← | ← | ← |
| Peroxidase (kU) | 4 | ← | ← | ← | ← | ← | ← | ← |

TABLE 1-continued

| Formulation of Test Papers | | | | | | | | |
|---|---|---|---|---|---|---|---|---|
| | Formulation No. | | | | | | | |
| | 1 | 2 | 3 | 4 | 5 | 6 | 7 | 8 |
| DAOS*[1] (g) | 1.0 | ← | ← | ← | — | — | — | — |
| Sodium iodate (mg) | 500 | ← | ← | ← | ← | ← | ← | ← |
| Citrate buffer, M: | 0.25 | ← | 0.25 | ← | 0.25 | ← | 0.75 | ← |
| (100 ml)  pH | 6 | | 4.5 | | 5 | | 4 | |

[Absorbed by Toyo Filter Paper No. 514A and dried at 50° C. for 60 min.]

(Second layer)

| | | | | | | | | |
|---|---|---|---|---|---|---|---|---|
| Thallium acetate (g) | 0 | 5.0 | 0 | 5.0 | 0 | 5.0 | 0 | 5.0 |
| 4-Aminoantipyrine (g) | 1.0 | ← | ← | ← | — | — | — | — |
| Tween 20 (ml) | 0.5 | ← | ← | ← | ← | ← | ← | ← |
| TMBZ*[2] (g) | — | — | — | — | 1.0 | ← | ← | ← |
| Ethanol (ml) | 100 ml | ← | ← | ← | ← | ← | ← | ← |

[Dried at 50° C. for 50 minutes]

(An indicator was a combination of 4-aminoantipyrine and DAOS or TMBZ alone.)
Note
*[1]Sodium N-ethyl-N-(2-hydroxy-3-sulfopropyl)-3,5-dimethoxyaniline.
*[2]3,3',5,5'-Tetramethylbenzidine.

EXAMPLE 2

With a test paper for detecting occult blood, the same tests as in Example 1 were carried out. The formulation of the test paper was as follow:

FIRST LAYER

The following mixture was absorbed by a filter paper (Toyo Filter Paper No. 514A) and dried at 80° C. for 30 minutes for form a first layer:
  50 ml of 1.5 M citrate buffer (pH 4)
  20 ml of purified water
  30 ml of ethanol
  300 mg of sodium laurylsulfate
  2 ml of cumene hydroperoxide
  3.0 g or 0 g (comparison) of thallium sulfate Then, the following mixture was coated on the first layer and dried at 50° C. for 30 minutes:
  50 ml of purified water
  50 ml of acetone
  1.0 g of 3-aminoquinoline
  500 mg of o-tolidine
  500 mg of sodium iodate The change of the background was measured by the same procedures as in Example 1.

The sensitivity was examined by the same manner as in Example 1 but using, as a sample, a hemoglobin solution (concentration: 0, 0.05, 0.1 or 1 mg/dl).

The change of the reflectance was examined by the same procedures as in Example 1 but using, as a sample, a solution of hemoglobin having a concentration of 0, 0.05, 0.1 or 1 mg/dl to which ascorbic acid was added at a concentration of 0, 20, 100 or 250 mg/dl.

Figure 4:
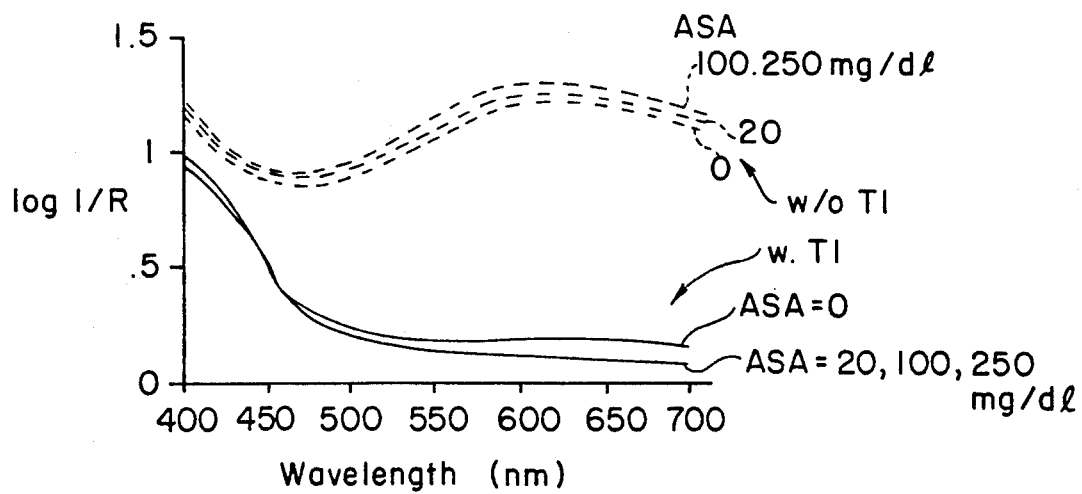
FIG. 4 is a graph showing the change of the background by ascorbic acid in Example 2.
Figure 5:
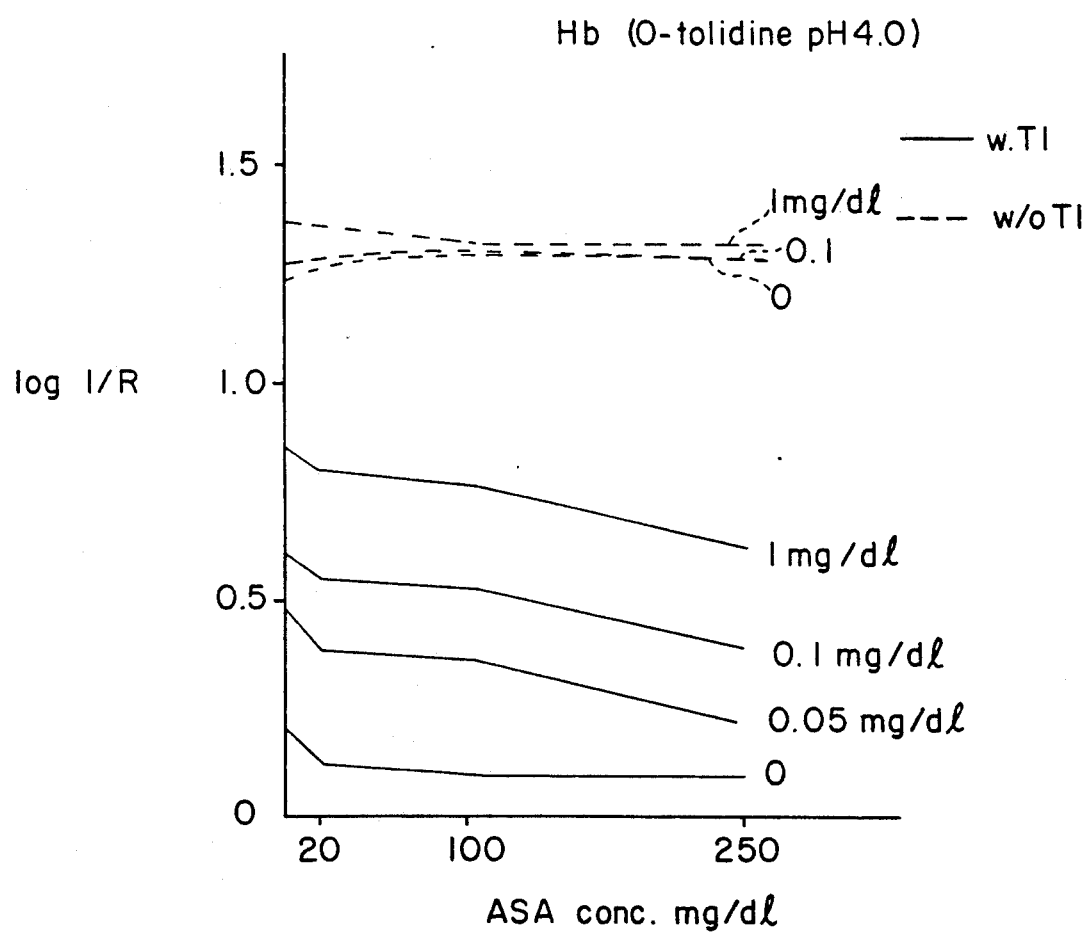
FIG. 5 is a graph showing the change of reflectance by ascorbic acid in Example 2.

The results are shown in FIG. 4, Table 2 and FIG. 5, respectively. In FIG. 4, the vertical axes is in terms of LogI/R.

TABLE 2

| Results of Sensitivity Measurement | | | | | |
|---|---|---|---|---|---|
| Thallium compound | Yes | | | | No |
| Hb amount (mg/dl) | 0 | 0.05 | 0.1 | 1.0 | 0 |
| LogI/R | 0.209 | 0.464 | 0.617 | 0.845 | 1.232 |

Wavelength for measurement: 640 nm.

What is claimed is:

1. An agent composition for detecting a redox reaction, comprising a redox reagent system, iodic acid or an iodate, and a monovalent thallium compound.

2. The agent composition according to claim 1, wherein said thallium compound is a salt of thallium with an inorganic or organic acid.

3. The agent composition according to claim 1, wherein said thallium compound is selected from the group consisting of thallium (I) chloride, thallium (I) sulfate and thallium (I) acetate.

4. The agent composition according to claim 1, wherein said iodate is selected from the group consisting of potassium iodate, sodium iodate, magnesium iodate and ammonium iodate.

5. A composition for detecting a redox reaction, comprising glucose oxidase, peroxidase, a color reagent, iodic acid or an iodate, and a monovalent thallium compound.

6. The composition according to claim 5, wherein said thallium compound is a salt of thallium with an inorganic or organic acid.

7. The composition according to claim 5, wherein said thallium compound is selected from the group consisting of thallium (I) chloride, thallium (I) sulfate and thallium (I) acetate.

8. The composition according to claim 5, wherein said iodate is selected from the group consisting of potassium iodate, sodium iodate, magnesium iodate and ammonium iodate.

9. The composition according to claim 5, wherein said composition is carried in dry form on a paper support.

10. A composition for detecting a redox reaction, comprising cumene hydroperoxide, o-tolidine, a color reagent, iodic acid or an iodate, and a monovalent thallium compound.

11. The composition according to claim 10, wherein said thallium compound is a salt of thallium with an inorganic or organic acid.

12. The composition according to claim 10, wherein said thallium compound is selected from the group consisting of thallium (I) chloride, thallium (I) sulfate and thallium (I) acetate.

13. The composition according to claim 10, wherein said iodate is selected from the group consisting of potassium iodate, sodium iodate, magnesium iodate and ammonium iodate.

14. The composition according to claim 10, wherein said composition is carried in dry form on a paper support.

* * * * *